United States Patent
Okamoto et al.

(10) Patent No.: US 6,994,701 B2
(45) Date of Patent: Feb. 7, 2006

(54) CORNEAL-ABLATION-AMOUNT DETERMINING APPARATUS AND A CORNEAL SURGERY APPARATUS

(75) Inventors: Keiki Okamoto, Hamamatsu (JP); Hiroyuki Hiramatsu, Hoi-gun (JP)

(73) Assignee: Nidek Co., Ltd., (JP)

( * ) Notice: Subject to any disclaimer, the term of this patent is extended or adjusted under 35 U.S.C. 154(b) by 25 days.

(21) Appl. No.: 10/464,536

(22) Filed: Jun. 19, 2003

(65) Prior Publication Data

US 2003/0236516 A1 Dec. 25, 2003

(30) Foreign Application Priority Data

Jun. 24, 2002 (JP) ............... 2002-183526

(51) Int. Cl.
A61B 18/18 (2006.01)
(52) U.S. Cl. ............... 606/5; 606/4; 128/898; 351/212
(58) Field of Classification Search ............... 606/4–6, 606/10–12; 128/898; 351/208–211
See application file for complete search history.

(56) References Cited

U.S. PATENT DOCUMENTS

| | | | |
|---|---|---|---|
| 4,732,148 A | | 3/1988 | L'Esperance, Jr. |
| 5,445,633 A | * | 8/1995 | Nakamura et al. ............... 606/5 |
| 5,507,799 A | * | 4/1996 | Sumiya ............... 606/5 |
| 5,520,679 A | | 5/1996 | Lin |
| 5,613,965 A | | 3/1997 | Muller |
| 5,637,109 A | | 6/1997 | Sumiya |
| 5,800,424 A | * | 9/1998 | Sumiya ............... 606/4 |
| 5,827,264 A | | 10/1998 | Hohla |
| 5,843,070 A | * | 12/1998 | Cambier et al. ............... 606/5 |
| 5,849,006 A | * | 12/1998 | Frey et al. ............... 606/5 |
| 5,904,678 A | | 5/1999 | Pop |

(Continued)

FOREIGN PATENT DOCUMENTS

EP 0 346 116 A2 12/1989

OTHER PUBLICATIONS

European Search Report dated Oct. 2, 2003.

*Primary Examiner*—A. Farah
(74) *Attorney, Agent, or Firm*—Rader, Fishman & Grauer PLLC

(57) ABSTRACT

A corneal surgery apparatus capable of reducing parts where a corneal curvature suddenly varies, and an apparatus for determining a corneal ablation amount. The corneal-ablation-amount determining apparatus includes a data input unit which inputs data on a correction amount of a patient's eye and data on a size of a second ablation zone for connecting a first ablation zone for securing the correction amount with a non-ablation area, a calculation unit which divides the inputted correction amount into at least ten, obtains an ablation amount for each divided correction amount as a lens component is ablated according to a size gradually enlarged from the first ablation zone to an outer diameter of the second ablation zone for each divided correction amount, and determines a total ablation amount by summing each obtained ablation amount, and an output unit which outputs data on the determined ablation amount.

3 Claims, 6 Drawing Sheets

U.S. PATENT DOCUMENTS

| | | |
|---|---|---|
| 5,906,608 A * | 5/1999 | Sumiya et al. ................. 606/5 |
| 5,907,388 A | 5/1999 | Fujieda |
| 5,984,916 A * | 11/1999 | Lai ............................ 606/11 |
| 6,033,075 A | 3/2000 | Fujieda et al. |
| 6,203,539 B1 | 3/2001 | Shimmick et al. |
| 6,325,792 B1 * | 12/2001 | Swinger et al. ................ 606/4 |
| 6,467,907 B1 | 10/2002 | Fujieda et al. |
| 6,585,723 B1 * | 7/2003 | Sumiya ........................ 606/5 |
| 6,663,619 B2 * | 12/2003 | Odrich et al. .................. 606/5 |
| 6,923,802 B2 * | 8/2005 | Williams et al. ............... 606/5 |

* cited by examiner

|  | Correction Amount (D) | OZ (mm) | TZ (mm) |
|---|---|---|---|
| Stage1 | S-1.50 | 4.5 | 7.0 |
| Stage2 | S-1.50 | 5.5 | 8.0 |
| Stage3 | S-2.00 | 6.5 | 9.0 |

OZ=Size of Optical Zone

TZ=Size of Transition Zone added to the outside of Optical Zone

FIG. 9

CORNEAL-ABLATION-AMOUNT DETERMINING APPARATUS AND A CORNEAL SURGERY APPARATUS

BACKGROUND OF THE INVENTION

1. Field of the Invention

The present invention relates to a corneal surgery apparatus for ablating a cornea by irradiating a laser beam and an apparatus for determining a corneal ablation amount.

2. Description of Related Art

There is known a corneal surgery apparatus which ablates a cornea by irradiating a laser beam and changes a shape of the cornea in order to correct a refractive error of an eye. The apparatus of this kind ablates part of the cornea so as to remove a lens component corresponding to a correction amount from the cornea. At this time, when only an optical region (hereinafter referred to as an "optical zone") which secures the correction amount is ablated, a boundary between an ablation area and a non-ablation area appears as a height difference. Therefore, in order to smoothly connect (join) the optical zone and the non-ablation area, the applicant has proposed, in Japanese Patent Application Unexamined Publication No. Hei6-189999 corresponding to U.S. Pat. No. 5,445,633, a method for forming an adjustment region (hereinafter referred to as a "transition zone") outside the optical zone. By way of example, in the case of a myopic correction, a transition zone is determined by obtaining a circle inscribed in both of pre-operative and post-operative corneal shapes.

Further, in the case of a spherical correction or cylindrical correction of high degree of myopia, as one method for avoiding an ablation depth from being deep (great), a method of dividing the correction amount into a plurality of amounts and changing each ablation size (diameter) is performed. By way of example, as shown in FIG. 9, for a patient's eye (eye to be operated on) of which a spherical correction of myopia is S-5.00D (diopter), a method of dividing the correction amount into three stages is performed.

As described in Japanese Patent Application Unexamined Publication No. Hei6-189999 corresponding to U.S. Pat. No. 5,445,633, owing to the formation of the transition zone outside the optical zone, the height difference at the boundary between the ablation area and the non-ablation area is reduced, and a favorable result is obtained. However, according to the method provided in Japanese Patent Application Unexamined Publication No. Hei6-189999 corresponding to U.S. Pat. No. 5,445,633, especially in the case where the correction amount is large, a radius of the circle inscribed in both of pre-operative and post-operative corneal shapes becomes small, and a number of parts where a corneal curvature suddenly varies are tend to appear over a wide range of the transition zone. If there are a number of parts where the corneal curvature suddenly varies, there is a problem that they cause a glare or a halo in night vision.

Also, in the method as shown in FIG. 9, there is a tendency of that the corneal curvature suddenly varies at the boundary of each of the stages. In addition, since it is necessary to manually input the correction amount and the ablation size (diameter) for each of the stages, there are such problems of that the inputting is laborsome, an error in inputting is apt to occur, the number of the divided stages is limited because of the manual inputting, an appropriateness of inputting depends on experiences of an operator, and the like. Furthermore, there is a problem of that, in the case of a surgery divided into a plurality of the stages, surgical time becomes longer.

SUMMARY OF THE INVENTION

An object of the invention is to overcome the problems described above and to provide a corneal surgery apparatus capable of reducing parts where a corneal curvature suddenly varies in an ablation area and an apparatus for determining a corneal ablation amount, with simple methods.

To achieve the objects and in accordance with the purpose of the present invention, a corneal-ablation-amount determining apparatus includes a data input unit which inputs data on a correction amount of a patient's eye and data on a size of a second ablation zone for connecting a first ablation zone for securing the correction amount with a non-ablation area, a calculation unit which divides the inputted correction amount into at least ten, obtains an ablation amount for each divided correction amount as a lens component is ablated according to a size gradually enlarged from the first ablation zone to an outer diameter of the second ablation zone for each divided correction amount, and determines a total ablation amount by summing each obtained ablation amount, and an output unit which outputs data on the determined ablation amount.

In another aspect of the present invention, a corneal surgery apparatus for ablating a cornea of a patient's eye by irradiating a laser beam includes an irradiating optical system for irradiating a laser beam onto the cornea, a data input unit which inputs data on a correction amount of the patient's eye, and data on a size of a second ablation zone for connecting a first ablation zone for securing the correction amount with a non-ablation area, a calculation unit which divides the inputted correction amount into at least ten, obtains an ablation amount for each divided correction amount as a lens component is ablated according to a size gradually enlarged from the first ablation zone to an outer diameter of the second ablation zone for each divided correction amount, and determines a total ablation amount by summing each obtained ablation amount, and a control unit which controls the irradiation based on data on the determined ablation amount.

Additional objects and advantages of the invention are set forth in the description which follows, are obvious from the description, or may be learned by practicing the invention. The objects and advantages of the invention may be realized and attained by the corneal-ablation-amount determining apparatus and corneal surgery apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 9 is a view illustrating an example of a conventional method for dividing the correction amount into a plurality of amounts.

DETAILED DESCRIPTION OF THE PREFERRED EMBODIMENTS

Figure 1:
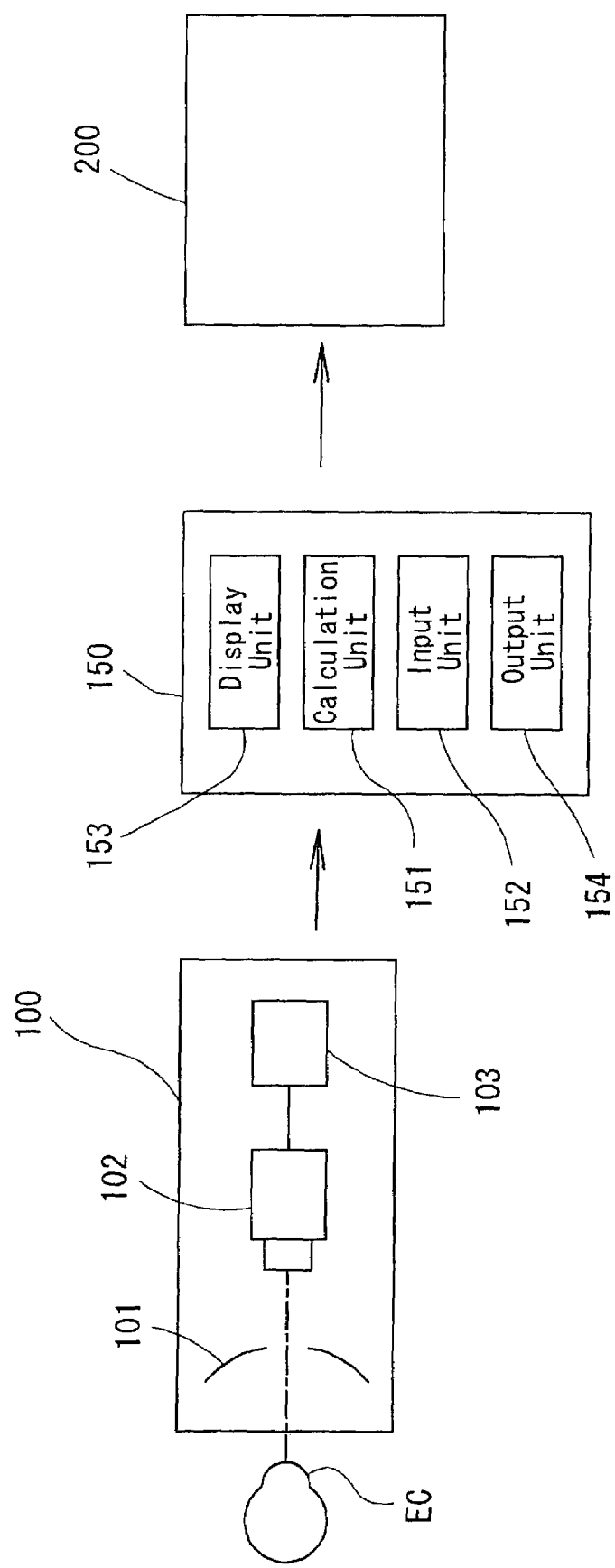
FIG. 1 is a block diagram showing a schematic configuration of a corneal surgery apparatus system consistent with the present invention.

A detailed description of one preferred embodiment of a corneal-ablation-amount determining apparatus and a corneal surgery apparatus embodied by the present invention is provided below with reference to the accompanying drawings. FIG. 1 is a block diagram showing a schematic configuration of a corneal surgery apparatus system consistent with the present invention.

A corneal-shape measurement apparatus 100 obtains data on the corneal shape of a patient's eye (eye to be operated on) being a factor for determining a corneal ablation amount. The measurement apparatus 100 is provided with projecting means 101 for projecting a number of annular placido rings onto a cornea EC of the patient's eye, image pickup means 102 for picking up images of the rings, and detecting means 103 for processing the picked up images to detect edges of the ring images and obtaining a corneal curvature distribution over a wide range.

A calculation apparatus 150 calculates the corneal ablation amount and is provided with a calculation unit 151, an input unit 152, a display unit 153 such as a display, a data output unit 154, and the like. A commercially available personal computer may be used for them. The data on the corneal shape obtained by the measurement apparatus 100 is inputted by the input unit 152 via cable communication or storage media such as a flexible disk. In addition, data on a size (diameter) of an ablation area, data on a correction amount and the like are inputted by the input unit 152. A calculation result on the ablation amount is graphically displayed on the display unit 153.

A corneal surgery apparatus 200 ablates the cornea by irradiating a laser beam and is provided with an input unit which inputs the data on the ablation amount obtained by the calculation apparatus 150 via cable communication or storage media such as a flexible disk.

Figure 2:
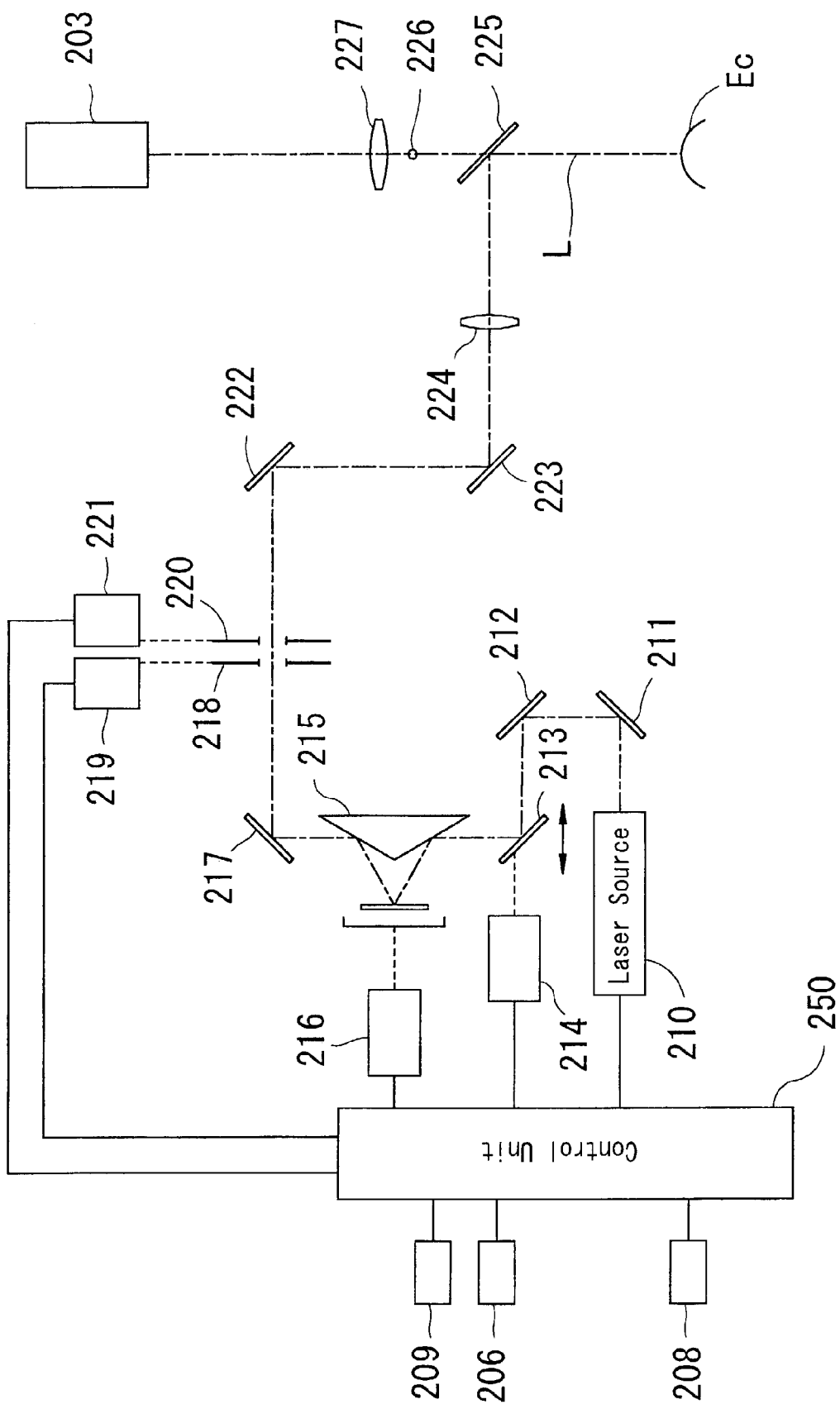
FIG. 2 is a view showing a schematic configuration of an irradiation optical system and a control system of a corneal surgery apparatus.

FIG. 2 is a view showing a schematic configuration of an irradiation optical system and a control system in the corneal surgery apparatus 200. Reference numeral 210 is a laser source for emitting an excimer laser beam with a wavelength of 193 nm. The laser beam emitted from the laser source 210 is reflected by mirrors 211 and 212, and further reflected by a plane mirror 213. The mirror 213 is movable in a direction of the arrow shown in FIG. 2 by a mirror driving unit 214, and is capable of ablating an object uniformly by translating the laser beam in the Gaussian distribution direction. (As Japanese Patent Application Unexamined Publication No. Hei4-242644 corresponding to U.S. Pat. No. 5,507,799 describes this point in detail, please refer to it).

Reference numeral 215 is an image rotator which is rotatably driven about a central optical axis L by an image rotator driving unit 216, and rotates the laser beam about the optical axis L. Reference numeral 217 is a mirror.

Reference numeral 218 is a circular aperture having a circular opening for limiting the ablation area to a circular shape, and an aperture driving unit 219 varies a diameter of the circular opening. Reference numeral 220 is a slit aperture having a slit opening for limiting the ablation area to a slit shape, and an aperture driving unit 221 varies opening width and direction of the slit opening. Reference numerals 222 and 223 are mirrors for changing a direction of the beam. Reference numeral 224 is a projecting lens for projecting the openings of the circular aperture 218 and the slit aperture 220 onto the cornea Ec.

Reference numeral 225 is a dichroic mirror having a property of reflecting an excimer laser beam and transmitting visible light. The laser beam passed through the projecting lens 224 is reflected by the dichroic mirror 225 and directed to and irradiated onto the cornea Ec. Placed above the dichroic mirror 225 are a fixation light 226, an objective lens 227, and a microscope unit (observation unit) 203.

Reference numeral 250 is a control unit which controls the laser source 210, each of the driving units and the like. In addition, the control unit 250 is connected with a foot switch 208, a variety of operation switches, a controller 206 for moving, with respect to the patient's eye, an arm in which the irradiation optical system are disposed, and a computer 209. The computer 209 is provided with an input unit which inputs surgical data such as the data on the ablation amount, and a display unit, and performs calculation, display, storage and the like of data for irradiation control based on the surgical data.

Corrective surgery performed by the corneal surgery apparatus 200 will be described hereinafter. In the case of a spherical correction of myopia, the control unit 250 exercises control based on the data for irradiation control as follows. 1) The laser beam is scanned (moved) in the Gaussian distribution direction within the opening of the circular aperture 218 by a movement of the mirror 213. 2) Every time the laser beam has scanned (moved) in one direction, the scanning (moving) direction of the laser beam is changed by the rotation of the image rotator 215 (e.g. three directions having a spacing of 120 degrees) to perform approximately uniform ablation within the opening of the circular aperture 218. 3) The processes 1) and 2) are performed every time the opening diameter of the circular aperture 218 is sequentially changed. According to these processes, ablation may be performed on a spherical component which is deep at a central part of the cornea and shallow at a peripheral part.

In the case of a cylindrical correction of myopia, the control unit 250 exercises control based on the data for irradiation control as follows. 1) The opening diameter of the circular aperture 218 is aligned with an optical zone. 2) The opening direction of the slit aperture 220 is adjusted so that its opening width varies in a steepest meridian direction. 3) As with the aforementioned spherical correction, the laser beam is scanned (moved) in the Gaussian distribution direction within the opening of the slit aperture 220 by a movement of the mirror 213. 4) Every time the laser beam has scanned (moved) in one direction, the scanning (moving) direction of the laser beam is changed by the rotation of the image rotator 215, to perform approximately uniform ablation within the opening of the slit aperture 220. 5) The processes 3) and 4) are performed every time the opening width of the slit aperture 220 is sequentially changed. According to these processes, ablation of a cylindrical component may be performed.

Figure 3:
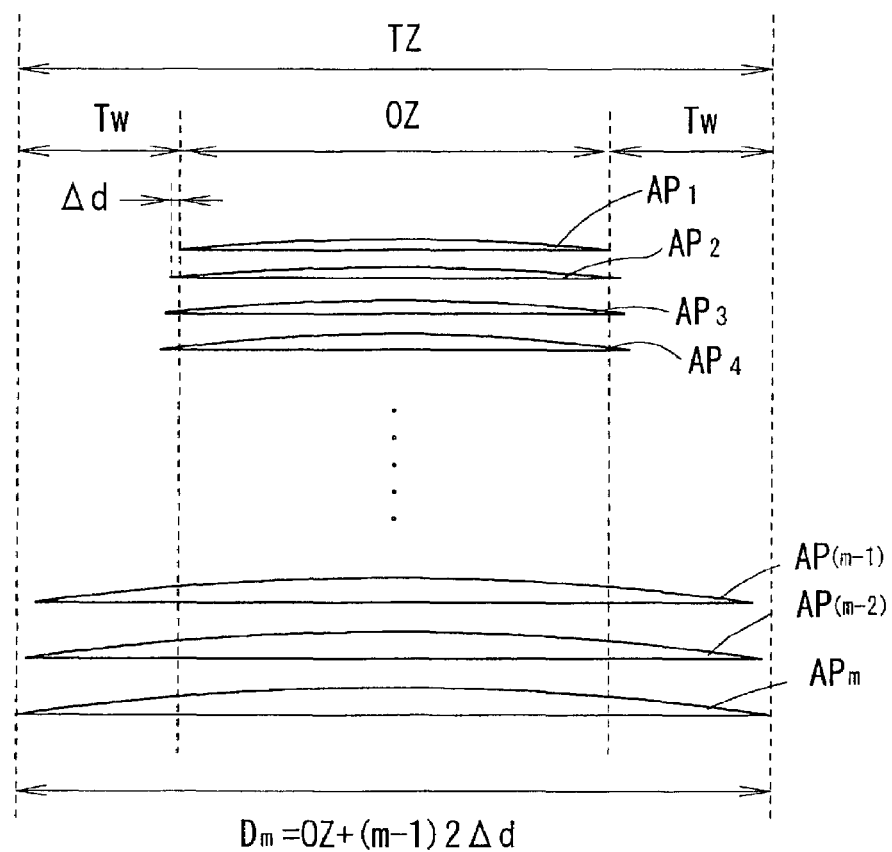
FIG. 3 is a view illustrating a formation of a transition zone in the case of a spherical correction of myopia.

Next, a formation of a transition zone which connects the optical zone for securing a correction amount and a non-ablation area will be described hereinafter. Firstly, the case of the spherical correction of myopia will be described, referring to FIGS. 3 to 5. Incidentally, a pre-operative corneal shape (corneal curvature distribution) obtained by the measurement apparatus 100, an objective correction amount (diopter) for the patient's eye, a size (diameter) (OZ) of the optical zone, and a size (diameter) (TZ) of the transition zone which is added to the outside of the optical zone are previously inputted to the calculation apparatus 150 by the input unit 152. The ablation amount is calculated by the calculation unit 151.

Firstly, the size (width) Tw of the transition zone determined based on OZ and TZ is divided with an infinitesimal interval $\Delta d$. Tw is obtained by inputting OZ and TZ, but the value of Tw may be directly inputted. A divisional number m is given by an expression; $m = Tw/\Delta d + 1$. For example, in the case of OZ=5 mm, TZ=9 mm, and $\Delta d=0.02$ mm, then m=101 is obtained. When the correction amount Pc (diopter) is minutely divided with the divisional number m, then $Pc = P_1 + P_2 + P_3 + \ldots + P_m$ is obtained. Hereinafter, the divided correction amounts $P_1, P_2, P_3, \ldots P_m$ will be represented as $P_M$ (M=1, 2, 3, ..., m).

Next, the following description is based on a concept that the ablation of the spherical lens component is performed with respect to each $P_M$. The first ablation size (diameter) $D_1$ for $P_1$ initially OZ, and the ablation size (diameter) is sequentially increased by $2\Delta d$, that is to say, the second ablation size (diameter) $D_2 = OZ + 2\Delta d$, and the third ablation size (diameter) $D_3 = OZ + 4\Delta d$. The last m-th ablation size (diameter) $D_m$ is $OZ + (m-1)2\Delta d = TZ$. The M-th ablation size (diameter) $D_M$ is represented as $D_M = OZ + (M-1)2\Delta d \ldots$ (M=1, 2, 3, ..., m).

The ablation amount $AP_M$ (M=1, 2, 3, ..., m) for each $P_M$ is calculated. In this calculation, a post-operative corneal curvature $R_M$ when each $P_M$ is ablated from the pre-operative corneal curvature $R_{(M-1)}$ is given by the following expression 1. Besides, n represents a refractive index of the cornea, and n=1.376 is normally used.

$R_M = (n-1)R_{M-1}/((n-1) + R_{M-1} P_M)$  (expression 1)

Figure 4:
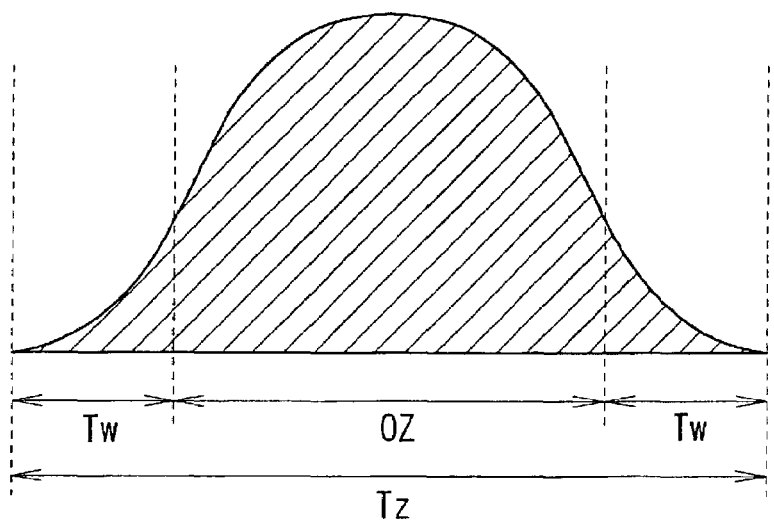
FIG. 4 is a view showing a total ablation amount obtained by summing each ablation amount in FIG. 3.
Figure 5:
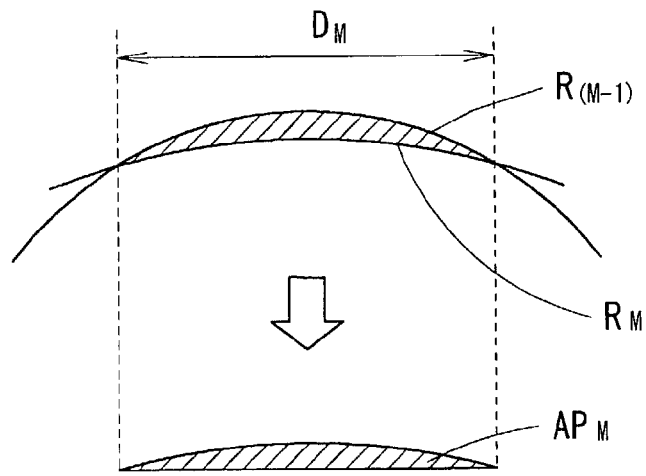
FIG. 5 is a view showing the ablation amount obtained with respect to each divided correction amount.

In addition, a difference between a curved shape of $R_M$ and that of $R_{M-1}$ is obtained within the range of $D_M$, whereby each ablation amount $AP_M$ (M=1, 2, 3, ..., m) for each $P_M$ (M=1, 2, 3, ..., m) is obtained (see FIG. 5). Finally, by accumulating (summing) each $AP_M$, the total ablation amount as shown in FIG. 4 is obtained.

When the expression 1 is expanded for $P_1, P_2, P_3, \ldots P_m$ respectively, the following expressions are obtained:

$P_1 = (1/R_1 - 1/R_0) * (n-1)$ $P_2 = (1/R_2 - 1/R_1) * (n-1)$ $P_3 = (1/R_3 - 1/R_2) * (n-1)$ $P_m = (1/R_m - 1/R_{m-1}) * (n-1)$ $R_0$ represents the pre-operative corneal curvature, and $R_m$ represents the ultimate corneal curvature when the ablation is performed in the correction amount $P_c$.

By summing all of the above expressions, the following expression is obtained:

$P_1 + P_2 + P_3 + \ldots + P_m = (1/R_m - 1/R_0) * (n-1)$

This indicates that the correction amount $P_c$ within the optical zone is secured.

Besides, on the outside of the optical zone, each ablation amount $AP_m$ (M=1, 2, 3, ..., m) is summed to consequently form the transition zone in a size (width) Tw which connects the optical zone with the non-ablation area. In the transition zone, the ablation amount is gradually reduced as the distance from the optical zone becomes greater, thus, parts (ranges) where the corneal curvature (tangential curvature) suddenly varies are reduced.

Figure 6:
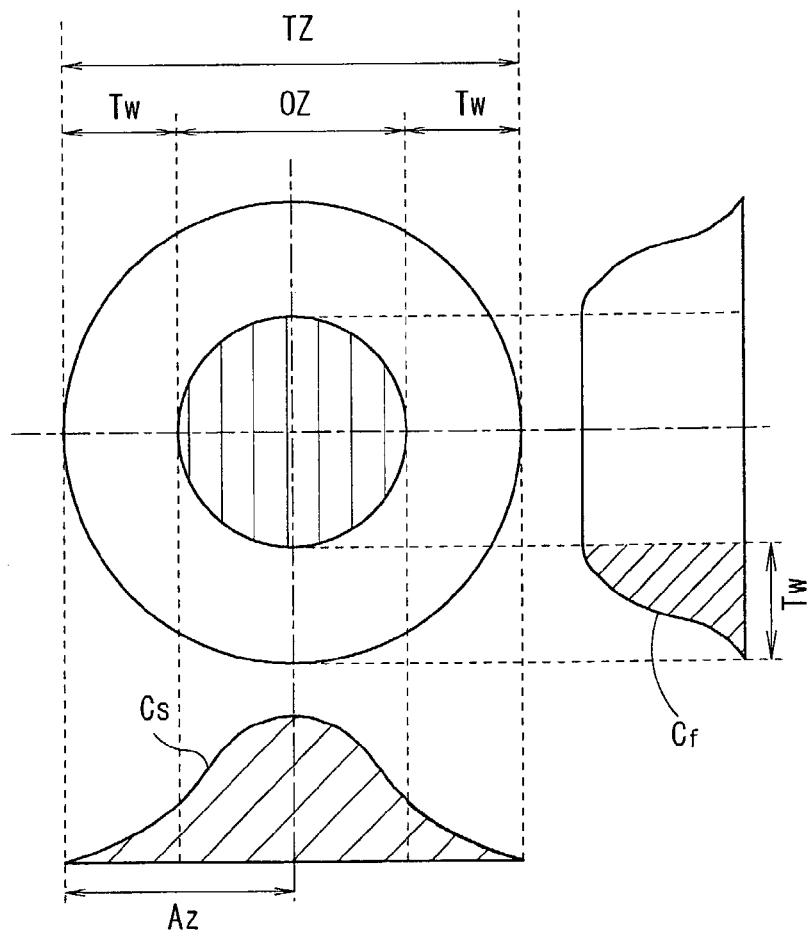
FIG. 6 is a view illustrating a formation of a transition zone in the case of a cylindrical correction of myopia.

Next, the case of the cylindrical correction of myopia will be described, referring to FIG. 6. As is the case with the spherical correction of myopia, in the ablation in the steepest meridian direction, the correction amount $P_c$ is minutely divided for ablation of the cylindrical lens component, and summation of each ablation amount is obtained. The ablation amount in the steepest meridian direction is $C_s$ in FIG. 6.

On the other hand, for the ablation in the flattest meridian direction, the ablation amount is uniform within the optical zone, and the ablation amount $C_f$ of the transition zone Tw utilizes the ablation amount $C_s$ in the steepest meridian direction. $C_f$ is obtained by converting $C_s$ for a radius Az of Tz into Tw. More specifically, $C_f$ is an ablation amount in which $C_s$ is compressed with Tw/Az in a width direction. Therefore, as the shape of the ablation amount in the steepest meridian direction is reflected to a shape of the transition zone in the flattest meridian direction, the parts where the corneal curvature suddenly varies may be reduced in the vicinity of the optical zone.

Incidentally, the larger the divisional number m is, the more minutely the gradually varying ablation amount is divided, and it is mathematically possible to reduce the sudden variation in the corneal curvature. As the divisional number m is determined based on Tw and $\Delta d$, it is increased when $\Delta d$ is made small. In the preferred embodiment of the present invention, a value of $\Delta d$ is determined based on a relationship with an ablation-diameter (width) resolution of the circular aperture 218 (the slit aperture 220 in the case of the cylindrical ablation), and the ablation-diameter (width) resolution on the cornea is 0.02 mm in radius. This is the value set for smoothing also the shape of the transition zone in the flattest meridian direction in the cylindrical correction of myopia. When only the shape of the transition zone in the steepest meridian direction in the spherical correction and cylindrical correction of myopia is taken into consideration, the value of $\Delta d$ may be larger than 0.02 mm, because the ablation depth of the transition zone is low.

Figure 7:
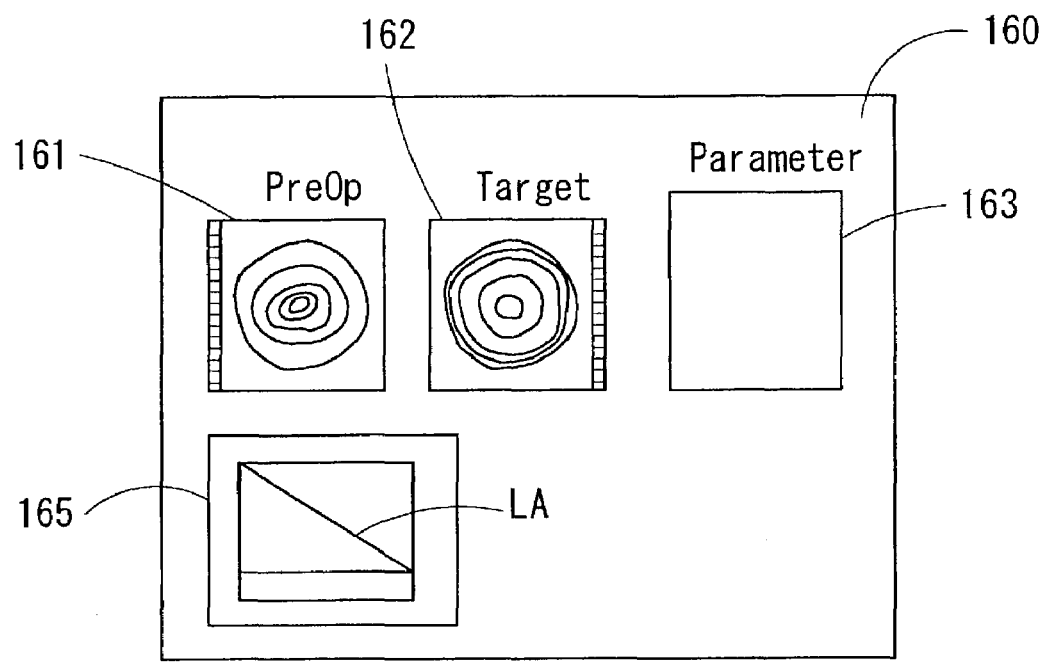
FIG. 7 is a view showing an example of a display provided on a display unit of a calculation apparatus.

The aforementioned calculation is processed by the calculation unit 151. The pre-operative corneal shape and an expected post-operative corneal shape are converted into corneal refractive power, and displayed on a display 160 of the display unit 153 as color maps of topography as shown in FIG. 7. Reference numeral 161 is a pre-operative color map and 162 is a post-operative color map. On a parameter section 163, the inputted data or the ablation depth data are displayed. Further, on a window display part 165, a parameter section for changing an ablation curve of the transition zone is displayed. The inputted data displayed on the parameter section 163 and the parameter of the ablation curve of the transition zone are changed, so that the expected post-operative corneal shape may be simulated, and a result thereof may be confirmed by the color map.

Figure 8:
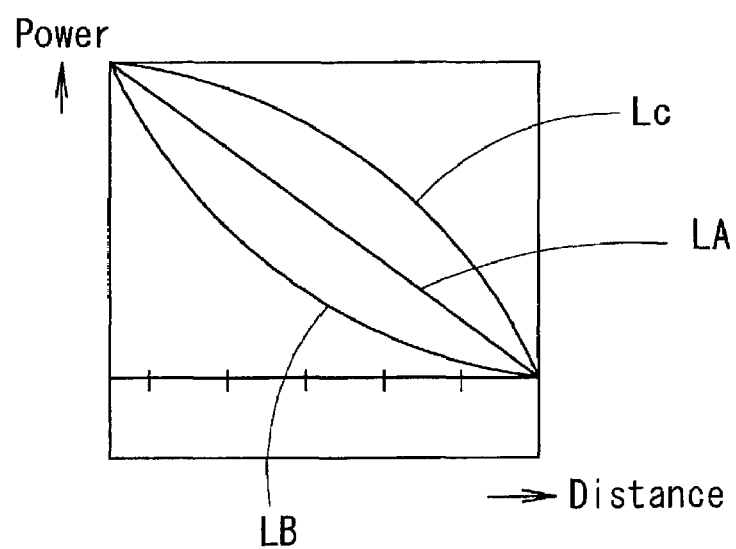
FIG. 8 is a view illustrating a method for changing an ablation curve of the transition zone.

FIG. 8 is a view illustrating a method for changing the ablation curve of the transition zone. In FIG. 8, the vertical axis represents the correction amount $P_C$ (a normalized value) and the horizontal axis represents the radius Az of Tz. A straight line LA shows the case where the divided correction amounts $P_M$ of the correction amount $P_C$ with respect to a distance in the diameter direction are made equal. A concave-curved line LB indicates the case where the divided correction amount $P_M$ of the correction amount $P_C$ is large near the center and is gradually made smaller toward the peripheral side. To the contrary, a convex-curved line LC indicates the case where the divided correction amount $P_M$ of the correction amount $P_C$ is small near the center and is gradually made larger toward the peripheral side. Where the line LC is set, the variation in the corneal curvature in the vicinity of the optical zone may be small, but a maximum ablation depth becomes great, as compared with the case where the line LA is set. When the line LB is set, the variation in the corneal curvature in the vicinity of the optical zone becomes large, but the maximum ablation depth becomes low, as compared with the case where the line LA is set. Therefore, the ablation curve and the maximum ablation depth of the transition zone may be adjusted by changing a pattern for minutely dividing the correction amount $P_C$.

The parameter of the line displayed on the window display part 165 may be changed using a mouse or the like included in the input unit 152. According to this change, the display of the post-operative color map 162 and the display of the ablation depth on the parameter section 163 are also changed. Owing to such simulation, the operator may select a curved shape of the transition zone suitable for a refractive correction of the patient's eye, while taking a relationship with the ablation depth into consideration. Incidentally, the lines LA, LB, and LC may be selected from a plurality of lines which are previously set, or they may be optionally settable.

The data on the ablation amount determined by the calculation apparatus 150 is inputted to the computer 209 of the corneal surgery apparatus 200. Besides, a function of calculating the ablation amount may be included in the corneal shape measurement apparatus 100 or the computer 209 of the corneal surgery apparatus 200. The control unit 250 of the corneal surgery apparatus controls the opening diameters and opening widths of the circular aperture 218 and slit aperture 220 based on the data for irradiation control, and causes the laser beam to be irradiated. The transition zone is formed by superimposing the scans with the laser beam while the opening diameter of the circular aperture 218 is sequentially changed from the optical zone to the outside.

As a result of ablation on a model eye and as a result of the simulation of ablation on a human eye, both performed by the present inventors according to the method for forming the transition zone as described above, it is confirmed that the parts (ranges) where the corneal curvature suddenly varies are reduced as compared with the conventional method. According to the above-mentioned method, the parts where the corneal curvature suddenly varies appear to some degree near the periphery of the transition zone, however, the parts where the corneal curvature suddenly varies are reduced in the vicinity of the optical zone for securing the correction amount. If a pupil does not expand over the periphery of the transition zone, a glare and a halo in night vision are less prone to appear.

Incidentally, the irradiation optical system of the corneal surgery apparatus 200 as shown in FIG. 2 has a constitution where the circular aperture 218 and the slit aperture 220 are employed, but the apparatus may perform ablation while scanning a laser beam formed into a small spot by a scanning optical system such as a galvano-mirror. In the case of this kind of irradiation optical system, as the transition zone Tw in the flattest meridian direction at the time of the cylindrical correction may be largely secured, it becomes possible to suppress the sudden variation in the corneal curvature in the flattest meridian direction.

As described above, according to the present invention, it is possible to reduce the parts within the ablation area where the corneal curvature suddenly varies, with simple methods.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A method for determining a corneal ablation amount of a patient's eye, the method comprising the steps of:
   inputting a correction amount of the eye, a first size of a first ablation zone for securing the correction amount, and a second size of an ablation area including the first ablation zone and a second ablation zone which is formed outside the first ablation zone and connects the first ablation zone with a non-ablation area;
   dividing the inputted correction amount into at least ten;
   determining respective ablation sizes corresponding to the divided correction amounts while gradually enlarging them within a range from the first size to the second size according to the number of the divided correction amounts;
   determining divided corneal ablation amounts based on the divided correction amounts and the corresponding ablation sizes respectively; and
   determining a total corneal ablation amount of the eye by summing the divided corneal ablation amounts.

2. The method according to claim 1, wherein the inputting step inputs the second size by inputting a size of the second ablation zone.

3. The method according to claim 1, wherein the dividing step divides the inputted correction amount in accordance with a set divisional proportion.

* * * * *